United States Patent

Pendergast et al.

[11] Patent Number: 5,233,060
[45] Date of Patent: Aug. 3, 1993

[54] ETHYLENE RECOVERY IN DIRECT-OXIDATION ETHYLENE OXIDE PROCESSES

[75] Inventors: John G. Pendergast; Wayne A. Turner, both of Baton Rouge; Harold B. Martin, Jr., Plaquemine; Stephen A. Noding, Brusly, all of La.

[73] Assignee: The Dow Chemical Company, Midland, Mich.

[21] Appl. No.: 930,249

[22] Filed: Aug. 13, 1992

[51] Int. Cl.$^5$ .................. C07D 301/08; C07D 301/10; C07D 301/32; C07D 303/04

[52] U.S. Cl. .................. 549/523; 549/534; 549/538

[58] Field of Search .................. 549/534, 538, 523

[56] References Cited

U.S. PATENT DOCUMENTS

| | | | |
|---|---|---|---|
| 2,653,952 | 9/1953 | Egbert | 549/538 |
| 3,176,445 | 4/1965 | Collins et al. | 55/58 |
| 3,266,221 | 8/1966 | Avery | 55/58 |
| 3,312,719 | 4/1967 | Hullstrung et al. | 549/534 |
| 3,665,678 | 5/1972 | Kammermeyer et al. | 55/60 |
| 3,733,368 | 5/1973 | Dodd et al. | 260/677 A |
| 3,745,092 | 7/1973 | Vanderwater | 203/42 |
| 3,833,477 | 9/1974 | Brugerolle et al. | 195/109 |
| 3,867,113 | 2/1975 | Foster et al. | 55/44 |
| 3,914,277 | 10/1975 | Wood | 260/465.3 |
| 4,184,855 | 1/1980 | Butwell et al. | 55/48 |
| 4,313,009 | 1/1982 | Lhonore et al. | 568/947 |
| 4,345,918 | 8/1982 | Meissner | 55/38 |
| 4,430,312 | 2/1984 | Eickmeyer | 423/223 |
| 4,511,381 | 4/1985 | Mehra | 62/17 |
| 4,525,180 | 6/1985 | Hirai et al. | 55/37 |
| 4,601,738 | 7/1986 | Mehra | 62/17 |
| 4,617,038 | 10/1986 | Mehra | 62/17 |
| 4,623,371 | 11/1986 | Mehra | 62/17 |
| 4,769,047 | 9/1988 | Dye | 55/26 |
| 4,774,222 | 9/1988 | Rashkin | 502/347 |
| 4,831,162 | 5/1989 | Nakajima et al. | 549/534 |
| 5,177,225 | 1/1993 | Ramschandran et al. | 549/534 |

*Primary Examiner*—Joseph E. Evans

[57] ABSTRACT

In a direct-oxidation ethylene oxide process of the type comprising a) reacting a feed gas stream including ethylene and a commercially-pure oxygen in one or more reactors and b) absorbing out ethylene oxide from the product stream from the one or more reactors in a first absorption zone, the improvement comprising recovering unreacted ethylene from an ethylene-rich argon purge gas stream via an absorber and a stripper in combination, recycling the recovered ethylene to the feed gas stream, and purging an ethylene-lean argon purge gas stream.

9 Claims, 2 Drawing Sheets

ETHYLENE RECOVERY IN DIRECT-OXIDATION ETHYLENE OXIDE PROCESSES

The present invention relates to a process for the production of ethylene oxide by direct oxidation, and to a process and apparatus for recovering ethylene from a purge or vent gas stream in a direct-oxidation process for recycle.

The direct-oxidation process for manufacturing ethylene oxide is well-known, and generally involves passing a feed gas containing ethylene and substantially pure oxygen over a supported silver catalyst under pressure and heat, whereby the ethylene and oxygen react to form ethylene oxide. Per-pass conversion is typically low (i.e., on the order of 5 to 25 percent), so that a substantial recycle stream is generally required. Given the size of the recycle stream, and despite the low levels (0.5 percent or less, typically) of such material in commercially-pure oxygen, it is necessary that an argon purge be established to prevent argon from the oxygen feed (argon is the principal impurity in commercially-pure oxygen supplies and an inert in the direct oxidation process) from building up in the process. This argon purge stream, like the feed and recycle streams, carries a substantial amount of ballast gases such as nitrogen and/or methane but also has a substantial enough ethylene content to make ethylene recovery from the purge stream economically desirable.

U.S. Pat. No. 4,769,047 to Dye (Dye) accordingly describes a process for recovering ethylene from a vent gas in a direct-oxidation process, wherein the vent or purge gas stream is passed through a first, activated carbon adsorption zone to remove most of the $C_3$ and higher hydrocarbons formed in the process reactors. Ethylene and carbon dioxide are then selectively adsorbed from the lower $C_3$ and higher-content purge gas stream by pressure swing adsorption onto crystalline zeolite molecular sieve bodies, and the ethylene and carbon dioxide are then separated by conventional methods, e.g., contact with aqueous monoethanolamine or hot potassium carbonate followed by aqueous ammonia treating and caustic scrubbing. The separated ethylene is compressed and recycled back to the feed to the primary reactors. Dye cites also U.S. Pat. Nos. 3,176,445 to Collins et al. and 3,266,221 to Avery for showing, respectively, that ethylene may be separated from carbon dioxide by contact with a crystalline zeolite molecular sieve material, and that pressure swing adsorption (onto crystalline aluminosilicate molecular sieves) may be used to recovery ethylene from an ethylene oxide reactor off-gas.

SUMMARY OF THE PRESENT INVENTION

The present invention employs an absorber/stripper combination to recover ethylene from an argon purge gas stream, rather than the pressure swing adsorption of Dye and the references described therein.

In one preferred embodiment of the present invention, the effluent from the reactor section of a direct oxidation ethylene oxide process is fed to a first absorption zone for removing ethylene oxide therefrom. The overhead from this first absorber is thereafter compressed, and at least a portion of this stream is sent to a second absorption zone to remove carbon dioxide therefrom An argon purge gas stream is derived from the carbon dioxide-lean absorber overheads from the second absorption zone, and this argon purge gas stream is sent to ethylene recovery Those portions of the overheads from the first, ethylene oxide absorption zone and the second, carbon dioxide absorption zones not sent to carbon dioxide recovery and to ethylene recovery, respectively, are recycled directly back to feed gas makeup for the reactor section.

In another, less preferred embodiment, the argon purge gas stream sent to ethylene recovery is derived directly from the carbon dioxide-containing overhead from the first, ethylene oxide absorption zone, so that ethylene recovery occurs on a first portion of the overhead from the first absorption zone while carbon dioxide recovery occurs on a second portion of such overhead.

DETAILED DESCRIPTION OF THE DRAWINGS

Figure 1:
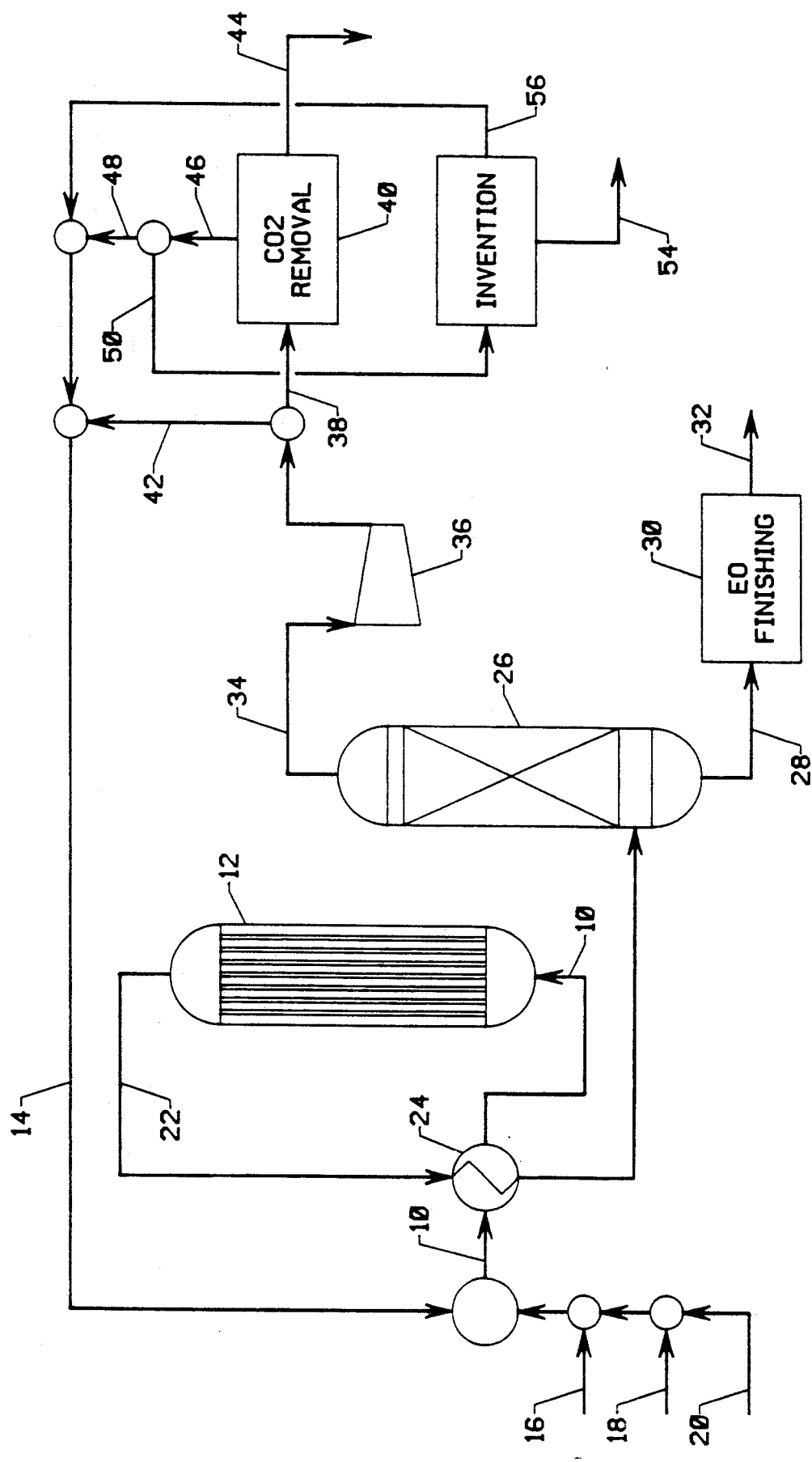
FIG. 1 is an overall schematic of a preferred direct oxidation ethylene oxide process of the present invention.

The direct oxidation ethylene oxide process of the present invention is illustrated schematically in a preferred embodiment in FIG. 1. For clarity of description, most of the pumps, compressors, heat exchangers, valves and miscellaneous process equipment are omitted from illustration or further description herein as routine and as not contributing to an understanding of the overall invention.

The feed gas stream 10 to the reactor section of the process, here exemplified by a single reactor 12, will typically consist of from about 5 to about 8 mole percent of oxygen, from about 10 to about 35 percent of ethylene, from about 3 to about 10 percent of carbon dioxide, from 0 to about 5 mole percent of ethane, from 0 to about 10 mole percent of argon and up to 80 percent of ballast gases such as nitrogen and/or methane, with methane being preferred to nitrogen. Trace quantities of reaction moderators, feed gas impurities and reaction by-products will also be present in the stream 10. The feed gas stream is constituted from a recycle stream 14, a fresh oxygen stream 16 (of a commercially-pure (95 to 99.5 percent) oxygen), a fresh ethylene (commercially-pure, 95 to 99 percent) feed stream 18 and a ballast gas stream 20. The bulk of feed gas stream 10, however, is formed by the recycle stream 14, with the ratio of recycle gas in stream 14 to fresh feed gases in streams 16, 18 and 20 being anywhere from about 10:1 up to about 40:1 (by volume).

Feed gas stream 10 is preheated by the effluent stream 22 from reactor 12 (via exchanger 24) prior to its introduction into the reactor 12. The preheated feed gas stream 10 is then fed into the reactor 12, wherein it is contacted with any of the conventionally-known supported silver catalysts useful for the direct oxidation process at temperatures ranging from about 200 to about 300 degrees Celsius and pressures of from about 200 to about 375 pounds per square inch, gauge (psig).

Some means of temperature control is incorporated in the process in conjunction with the reactor 12, to remove heat generated by the oxidation reaction of ethylene and oxygen to ethylene oxide and the competing oxidation side-reaction to carbon dioxide. The conversion rate of ethylene is thereby controlled as well as the selectivity to ethylene oxide (as opposed to carbon dioxide). Typical overall conversion rates of ethylene through the reaction section can range from about 7 to about 30 percent, while the selectivity of ethylene consumed to ethylene produced will normally be from about 72 to about 82 percent depending on work rate, the age of the catalyst employed, and other factors.

Depending on the selectivity of the particular catalyst employed, the ethylene conversion rate through the reactor 12, and the composition of feed gas stream 10, the effluent stream 22 from the reactor 12 will generally consist of from about 3 to about 6 mole percent of oxygen, from about 5 to about 30 mole percent of ethylene, from about 1-3 mole percent of ethylene oxide, from about 3.5 to about 12 mole percent of $CO_2$, and up to about 80 percent of ballast gases. The effluent stream 22, after being cooled in exchanger 24, is introduced into an ethylene oxide absorber tower 26, wherein the stream 22 is contacted with a conventional absorbent liquid for removing ethylene oxide from the stream 22. Typically cool absorber water may be used as the liquid absorbent.

The ethylene oxide-rich absorbent stream 28 from the bottom of the absorber 26 is pumped to an ethylene oxide finishing section 30 for recovery and purification of the ethylene oxide as stream 32. Trace quantities of other constituents of the stream 22 from the reactor 12 may also be absorbed into stream 28, and these may be recovered in the ethylene oxide finishing process and returned (not shown) to recycle stream 14. The technology for recovering and purifying the ethylene oxide from the absorbent stream 28 is generally well-known in the art, see, e.g., U.S. Pat. No. 3,745,092 to Vanderwater, and need not be discussed further for purposes of the present invention.

Following the absorption of ethylene oxide into the stream 28, the overhead stream 34 will typically consist of from about 3 to about 6 mole percent of oxygen, from about 5 to about 30 percent of unreacted ethylene, from about 4 to about 12 mole percent of carbon dioxide and part per million levels of ethylene oxide.

Some of the carbon dioxide in this stream is attributable to the recycle stream 14, with the remainder however being generated in the reaction zone in reactor 12. In order to prevent carbon dioxide from building up in the recycle stream 14 and in the feed stream 10, carbon dioxide is removed from the process at the same rate as it is produced in the reactor(s) 12. This is accomplished through recompression of stream 34 in compressor 36, followed by carbon dioxide removal from a suitably sized portion 38 of stream 34 in a $CO_2$ removal process 40, as for example by contact with a suitable carbon dioxide-selective absorbent. That portion of the overhead stream 34 not directed to the process 40 is recycled back to feed gas makeup as stream 42.

There are several known processes and absorbents for the removal of carbon dioxide from streams containing light hydrocarbons, oxygen and inert gases, see, e.g., U.S. Pat. Nos. 3,665,678 to Kammermeyer et al., 3,867,113 to Foster et al., and 4,184,855 to Butwell et al. The hot potassium carbonate process familiar to those skilled in the art is presently preferred. Typically the carbon dioxide-rich absorbate stream 44 from the process 40 will be from about 95 to about 99.9 percent pure (on a dry gas basis) in $CO_2$, and on a mass basis about 10 percent on average of the carbon dioxide in stream 34 will be removed from the process via stream 44. The remaining 90 percent will be recycled to the reactor(s) 12 via stream 42.

The carbon dioxide-lean absorber (combined) overhead 46 from the carbon dioxide removal process 40 typically consists of from about 3.3 to about 6.5 mole percent of oxygen, from about 5.5 to about 33.5 percent of ethylene, and the remainder of ballast gases. The overhead 46 is divided (like stream 34) between a stream 48 which is joined into recycle stream 14 and a stream 50 which is sent to an ethylene recovery process 52 shown in detail in FIG. 2, and from which an argon purge gas stream 54 is to be derived in addition to an ethylene-rich stream 56 to be recycled back into recycle stream 14. The stream 50 is conventionally sized so that the amount of argon removed ultimately therefrom in an argon purge gas stream 54 equals that amount added via the oxygen feed 16.

Figure 2:
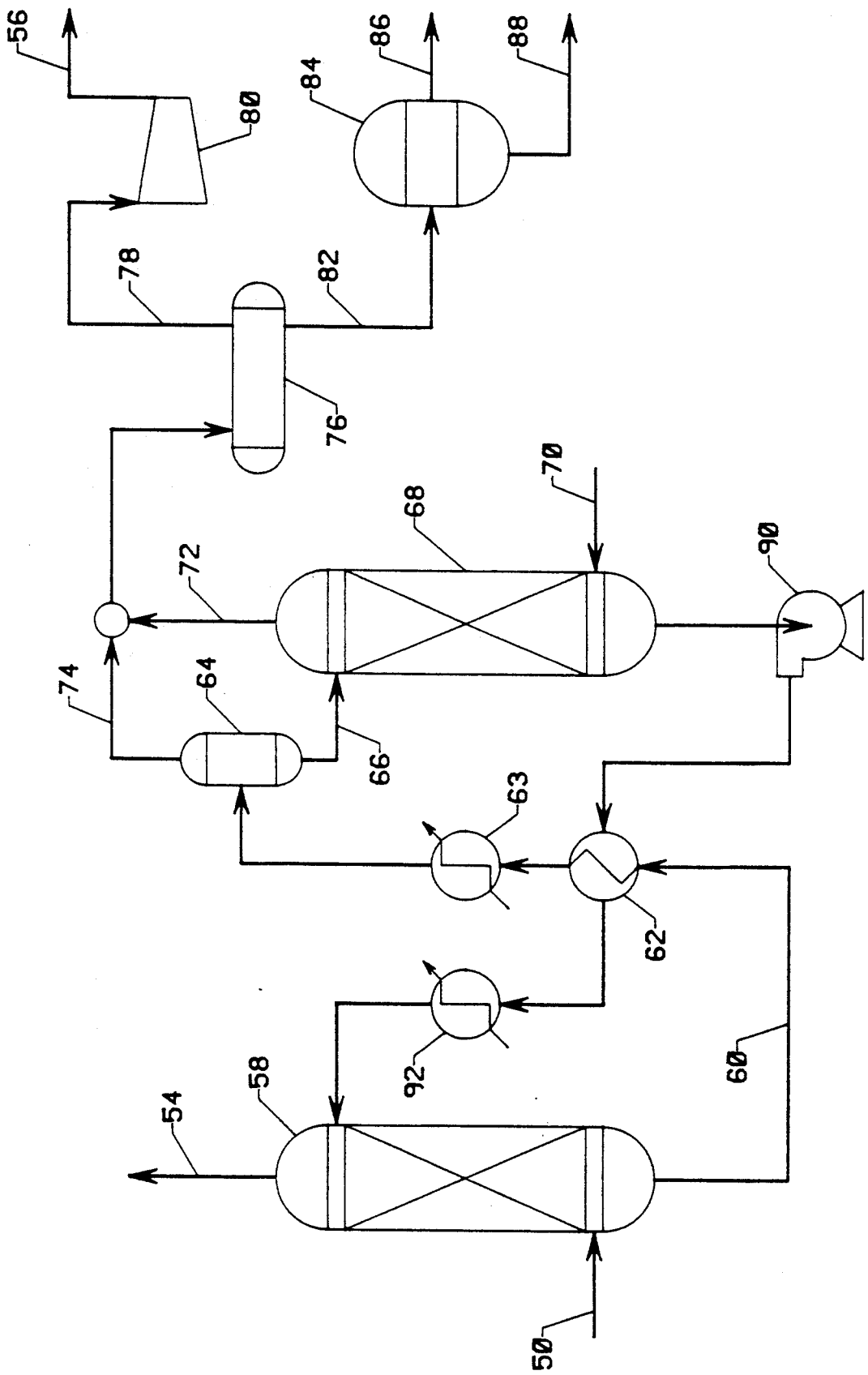
FIG. 2 depicts the "ethylene recovery" section of the process of FIG. 1 in a preferred configuration.

In FIG. 2, the stream 50 enters an absorber column 58, wherein ethylene is preferentially absorbed in a high molecular weight organic liquid. Suitably this high molecular weight organic liquid is n-dodecane, n-tridecane or some other normal paraffin or isoparaffin having an average molecular weight ranging from about 140 to about 212, or a combination of such paraffins or isoparaffins having an average molecular weight of from about 160 to about 220. A commercially-available material which has been found especially suitable is a mixture of $C_{10}$ to $C_{13}$ paraffins sold under the designation Norpar 12 TM (Exxon), and having an average molecular weight of 162. Mixtures of paraffins having a higher average molecular weight, and sold under the designations Norpar 13 TM and Norpar 15 TM (Exxon, respective molecular weights 186 and 212), are also suitable but less effective.

Liquid to gas flow rates for the absorber column 48 are generally on the order of 7:1 to 25:1 depending on column hydraulics, and the liquid loading factor is from about 10,000 to about 17,000, and especially about 15,000, pounds per square foot per hour. The contacting surface may be created by trays, structured packing or random dump packing, with the latter being preferred. Typical operating pressures and temperatures are from about 200 to about 350 pounds per square inch (gauge) and from about 10 to about 45 degrees Celsius, respectively.

The ethylene-lean absorber column overheads/argon purge gas stream 54 normally will contain from about 8 to about 15 mole percent of oxygen, about 0.1 to about 1.0 mole percent of ethylene, about 0.5 to about 2.0 mole percent of carbon dioxide and about 2 to about 10 mole percent of argon, with the remainder being ballast gases again. Stream 54 is conventionally incinerated prior to venting to the atmosphere.

The ethylene-rich absorbent stream 60 from the bottom of column 58 is heated in exchangers 62 and 63 and introduced into a flashing zone 64. The liquid bottoms 66 from the flashing zone 64 are thereafter introduced into a stripper 68, wherein the stream 66 is contacted with an inert gas stream 70 (preferably nitrogen or methane is used) at low pressures, e.g., 10 to about 54.7 lbs/sq. in. (gauge) and temperatures of from about 40 to about 80 degrees Celsius. Higher pressures could be employed with higher temperatures to keep the same relative volatilities of the absorbed gas and absorbent liquid from absorber column 58, however. The contacting surface for the stripper 68 can be created by trays, structured packing or random dump packing, with the latter being generally preferred. Liquid to gas flow ratio in the stripper 68 will typically be on the order of 200:1 up to about 400:1. Steam stripping could also be used, but is less preferred.

The overhead stream 72 from stripper 68 is combined with the flashed vapor stream 74 from flashing zone 64, and condensed in condenser 76 to produce an ethylene-rich overheads stream 78 containing from about 1 to about 10 mole percent of oxygen, from about 20 to about 45 mole percent of ethylene, from about 1.0 to about 30 mole percent of carbon dioxide, and the balance of ballast gases. This stream 78 is recompressed via compressor 80 and returned to recycle stream 14 as stream 56 (see FIG. 1), with preferably from about 90 to about 99 percent of the unreacted ethylene from reactor(s) 12 having been recovered in this fashion.

From about 10 to about 40 percent of the unreacted oxygen is recovered also. However, oxygen and argon have roughly the same affinity for the paraffinic absorbents for column 58 described above. Thus as more oxygen is recovered, either by increasing the flow rate of absorbent in column 58 or by using a cooler absorbent, more argon is returned to the system via recycle stream 14 and the purge flow through the stream 54 must be correspondingly increased. Given the comparative value of recovering additional oxygen versus the value of additional ethylene to be vented via the purge stream 54, it is presently considered that the amount of oxygen that is best recovered corresponds to whatever is incidentally recovered with optimal ethylene recovery.

The condensed liquid stream 82 from the condensor 76 is sent to a phase separator 84, wherein any condensed water is separated out as a waste stream 86 and the paraffinic hydrocarbon absorbent for column 58 is recovered as stream 88. The stream 88 of paraffinic hydrocarbon absorbent is combined with any necessary fresh absorbent, and pumped via pump 90 through heat exchangers 62 and 92 to cool the absorbent before it comes into contact with the stream 50 entering column 58.

Those skilled in the art will recognize that numerous changes may be made to the process described in detail herein, without departing in scope or spirit from the present invention as more particularly defined in the claims below.

What is claimed is:

1. In a direct-oxidation ethylene oxide process of the type comprising a) reacting a feed gas stream including ethylene and a commercially-pure oxygen in one or more reactors and b) absorbing out ethylene oxide from the product stream from the one or more reactors in a first absorption zone, the improvement comprising recovering unreacted ethylene from an ethylene-rich argon purge gas stream via an absorber and a stripper in combination, recycling the recovered ethylene to the feed gas stream, and purging an ethylene-lean argon purge gas stream.

2. An improved direct-oxidation ethylene oxide process as defined in claim 1, wherein the absorption of ethylene from the ethylene-rich argon purge gas stream includes contacting such stream with a high molecular weight organic liquid.

3. An improved direct-oxidation ethylene oxide process as defined in claim 2, wherein the high molecular weight organic liquid is n-dodecane, n-tridecane, a normal paraffin or isoparaffin other than n-dodecane or n-tridecane having a molecular weight of from about 140 to about 212, or a mixture of normal paraffins, of isoparaffins, or of normal paraffins and isoparaffins having an average molecular weight of between about 160 and about 220.

4. An improved direct-oxidation ethylene oxide process as defined in claim 1, wherein the ethylene absorber operates at temperatures between about 10 and about 45 degrees Celsius and at pressures between about 200 and about 350 psig.

5. An improved direct-oxidation ethylene oxide process as defined in claim 4, wherein the stripper associated with such absorber employs an inert gas as a stripping material and operates at pressures of from about 10 to about 54.7 psig and temperatures of from about 40 to about 80 degrees Celsius.

6. An improved direct-oxidation ethylene oxide process as defined in claim 5, wherein the inert gas is nitrogen or methane.

7. An improved direct-oxidation ethylene oxide process as defined in claim 1, wherein from about 90 to about 99 percent of the unreacted ethylene in the ethylene-rich argon purge gas stream is recovered and recycled back to the feed gas stream.

8. An improved direct-oxidation ethylene oxide process as defined in claim 1, further comprising recovering carbon dioxide from a compressed portion of the ethylene oxide-lean overhead stream from the first absorption zone in a second, carbon dioxide absorption zone, and wherein the ethylene-rich argon purge gas stream is derived from the carbon dioxide-lean absorber overheads from said second absorption zone.

9. An improved direct-oxidation ethylene oxide process as defined in claim 1, wherein the ethylene oxide-lean overhead stream from the first absorption zone has an ethylene content of from about 5 to about 30 mole percent, while following the recovery of ethylene from the ethylene-rich argon purge gas stream the ethylene content of gases purged is from about 0.1 to about 1.0 mole percent.

* * * * *